(12) United States Patent
Chen et al.

(10) Patent No.: US 8,076,070 B2
(45) Date of Patent: Dec. 13, 2011

(54) GENOME-WIDE CHROMOSOME CONFORMATION CAPTURE

(75) Inventors: Lin Chen, Los Angeles, CA (US); Reza Kalhor, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 219 days.

(21) Appl. No.: 12/537,138

(22) Filed: Aug. 6, 2009

(65) Prior Publication Data

US 2010/0081141 A1 Apr. 1, 2010

Related U.S. Application Data

(60) Provisional application No. 61/086,607, filed on Aug. 6, 2008.

(51) Int. Cl.
| | |
|---|---|
| C12Q 1/68 | (2006.01) |
| G01N 33/53 | (2006.01) |
| C12P 19/34 | (2006.01) |
| C07H 21/00 | (2006.01) |
| C07H 21/02 | (2006.01) |
| C07H 21/04 | (2006.01) |

(52) U.S. Cl. .......... 435/6; 435/7.1; 435/91.2; 536/22.1; 536/23.1; 536/24.3

(58) Field of Classification Search ............. 435/6, 7.1, 435/91.2; 536/22.1, 23.1, 24.3
See application file for complete search history.

(56) References Cited

U.S. PATENT DOCUMENTS

| | | | |
|---|---|---|---|
| 2003/0170689 A1* | 9/2003 | Stamatoyannapoulos et al. ................. | 435/6 |
| 2004/0096839 A1* | 5/2004 | Eberwine ................. | 435/6 |
| 2010/0081141 A1* | 4/2010 | Chen et al. ................. | 435/6 |
| 2010/0130373 A1* | 5/2010 | Dekker et al. ................. | 506/9 |

OTHER PUBLICATIONS

Bates et al., Crystal Structure of NFAT Bound to the HIV-1 LTR Tandem .kappa.B Enhancer Element. Structure 16 : 684-694 (2006).*
Dekker et al., Capturing chromosome conformation. Science 295 : 1306-1311 (2002).*
Dekker, J. The three C' s of chromosome conformation capture : controls, controls, controls. Nature Methods 3(1) :17-21 (2006).*
Dostie et al., Chromosome Conformation Capture Carbon Copy (5C): a massively parallel solution for mapping interactions between genomic elements. Genome Research 16 : 1299-1309 (2006).*
Dostie et al., Mapping networks of physical interactions between genomic elements using 5C technology. Nature Protocols 2(4) :988-1002 (2007).*
Gondor et al., High-resolution circular chromosome conformation capture assay. Nature Protocols 3 (2) :303-313 (Feb. 2008).*
Hagege et al., Quantitative analysis of chromosome conformation capture assays (3C-qPCR). Nature Protocols 2 (7) :1722-1733 (2007).*
Lamond et al., Structure and function in the nucleus. Science 280 :547-553 (1998).*
Meinkoth et al., Nick Translation Methods in Enzymology 152 : 91-94 (1987).*
Simonis et al., Nuclear organization of active and inactive chromatin domains uncovered by chromosome conformation capture-on-chip (4C). Nature Genetics 38 (11) : 1348-1354 (2006).*
Spilianakis et al., Interchromosomal associations between alternatively expressed loci. Nature 435 : 637-645 (2005).*
Splinter et al., 3C technology: analyzing the spatial organization of genomic loci in vivo. Methods in Enzymology 375 : 493-507 (2004).*
Wallace, DM., Large- and Small-scale Phenol Extractions. Methods in Enzymology 152 : 33-41 (1987).*
Zhao et al., Circular chromosome conformation capture (4C) uncovers extensive networks of epigenetically regulated intra- and interchromosomal interactions. Nature Genetics 38 (11) : 1341-1347 (2006).*
Dekker et al., Science 295: 1306 (2002).*
West et al., Human Molecular Genetics 14 (Review Is. 1) : R101-R111(2005).*
Spilianakis et al., Nature 435 : 637 (Jun. 2005).*

* cited by examiner

*Primary Examiner* — Ethan C Whisenant
(74) *Attorney, Agent, or Firm* — DLA Piper LLP (US)

(57) ABSTRACT

The invention relates to the use of GCC (Genome Conformation Capture) technology in determining the three dimensional arrangement of an entire genome.

15 Claims, 5 Drawing Sheets

5' Phos GCAGATCAATTAATACGATACCTGCGGACCGGTC 3' SEQ ID NO:1
3' TCGTCTAGTTAATTATGCTATGGACGC 5' SEQ ID NO:2

FIGURE 6

| Chr1:47592912-47593316 | LINKER | Chr12:5523470-5523656 |
| Chr2:153056757-153056980 | LINKER | Chr2:151406729-151406131 |
| Chr8:84095854-84096366 | LINKER | Chr8:100107717-100107818 |
| Chr5:92393492-92393860 | LINKER | Chr1:103448223-103448375 |

FIGURE 7

GENOME-WIDE CHROMOSOME CONFORMATION CAPTURE

RELATED APPLICATION

This application claims priority to U.S. Provisional Application Ser. No. 61/086,607, filed on Aug. 6, 2008, the content of which is incorporated herein by reference in its entirety.

FUNDING

This invention was made with government support under Contract No. R01 GM064642, R01 HL076334, and R01 GM077320 awarded by the National Institutes of Health. The government has certain rights in the invention.

FIELD OF THE INVENTION

The present invention relates to the use of GCC (Genome Conformation Capture) technology in determining the three dimensional arrangement of an entire genome.

BACKGROUND OF THE INVENTION

Three-dimensional arrangement of chromatin in the nucleus of eukaryotic cells is important in the regulation of gene expression. However, so far the methods that can address this arrangement of chromatin in the nucleus have been inefficient. Current methods are limited to assaying two select loci or loci that interact with one particular locus at a time, while being able to determine the spatial organization of all loci at the same time is highly demanded.

Since the 1980s fluorescence microscopy and related techniques have been used to study the overalls of nuclear architecture (Science 1998 Apr. 24; 280(5363):547-53). However, these techniques suffer from low resolution and low throughput. In 2002, Dekker and colleagues introduced the so-called 3C (Chromosome Conformation Capture) technology that allows for quantitative and higher resolution characterization of the spatial arrangement of loci relative to each other in a chromatin context (Science 2002; 295(5558):1306-11). This technique has been used to investigate the functional relevance of the spatial arrangement of loci relative to each other in many instances (e.g., Spilianakis C G et al. Nature 2005; 435(7042):637-45). Since 3C suffers low throughput (only two loci can be analyzed at a time), variations of this technology have been developed to improve efficiency. These variations are often referred to as 4C or 5C (Dostie J et al. Genome Res. 2006; 16(10):1299-309; Simonis M et al. Nat Genet. 2006; 38(11):1348-54; and Zhao Z et al. Nat Genet. 2006; 38(11):1341-7). All the mentioned techniques, in spite of improved throughput, are unable to solve the entire spatial arrangement of the chromatin in nucleus and therefore have to focus on capturing interaction partners of a limited number of loci.

SUMMARY OF THE INVENTION

The present invention is based, at least in part, upon the unexpected discovery that the GCC technology can be used in a method capable of capturing all the physical interactions of all different regions in chromatin in an unbiased fashion.

Accordingly, the invention features a method of determining the three-dimensional arrangement of an entire genome in a cell. The method comprises the following steps: (a) Contacting a cell with a cross-linking reagent (e.g., formaldehyde or other bi-functional cross-linking reagents that can covalently cross-link protein-protein and protein-DNA together) to cross-link the chromatin and the proteins in the cell. (b) Lysing the cell. (c) Digesting the chromatin with a restriction enzyme to generate DNA fragments with free ends. The DNA fragments are cross-linked to the proteins. (d) Ligating DNA linkers to all free DNA ends generated by the restriction enzyme. The DNA linkers may contain a palindromic overhang on one end and a T overhang on the other end. They may be ligated to the free DNA ends generated by the restriction enzyme through the T overhang, e.g., by T4 DNA ligase. In some embodiments, the method further comprises adjusting the ligation mixture after step (d) to highly favor intramolecular reactions. (e) Annealing the ends of the DNA linkers that are not ligated to the free DNA ends generated by the restriction enzyme. The ends of the DNA linkers being annealed are preferably adjacent due to the DNA linkers being ligated to the DNA fragments that are cross-linked to the proteins. (f) Translating the nicks between the annealed ends of the DNA linkers, e.g., with *E. coli* DNA polymerase I. The nicks may be translated in both directions along the DNA fragments until they arrive at cross-linked sites. In some embodiments, the method may further comprise adding phosphothioate-containing nucleotides to a second round of nick-translation. (g) Detaching the proteins cross-linked to the DNA fragments, e.g., by heating at 65° C. over night. (h) Extracting DNA, e.g., with phenol:chloroform. In some embodiments, the method further comprises removing DNA that has not gone through steps (d) and (e) and free DNA linkers after step (h), e.g., by a phosphothioate-sensitive exonuclease. (i) Subjecting the extracted DNA to two rounds of parallel sequencing, e.g., using the Illumina/Solexa platform. (j) Determining the three-dimensional arrangement of the entire genome in the nucleus of the cell.

Unless otherwise defined, all technical and scientific terms used herein have the same meaning as commonly understood by one of ordinary skill in the art to which this invention pertains. In case of conflict, the present document, including definitions, will control. The materials, methods, and examples disclosed herein are illustrative only and not intended to be limiting. Other features, objects, and advantages of the invention will be apparent from the description and the accompanying drawings, and from the claims.

BRIEF DESCRIPTION OF THE FIGURES

FIG. 6. Half linkers. This figure shows the sequence of a half-linker used in GCC. The half-linker has a palindromic 3' overhang on the top strand (SEQ ID NO:1) that allows annealing to a nearby half-linker at temperatures below its Tm. The top strand carries a 5' phosphate that makes complete ligation of the ends possible, without leaving any nicks. The bottom strand (SEQ ID NO:2) has a T overhang that will complement the A-overhang of target DNA ends during of T/A ligation. Multiple half-linker with identical 3' overhang and different double strand sequence can be used in one reaction.

FIG. 7. Example of the results obtained from four different molecules in the GCC library.

DETAILED DESCRIPTION OF THE INVENTION

GCC (Genome Conformation Capture) technology is meant to determine the three dimensional arrangement of the entire eukaryotic genome at once. Such a technology can be used to address fundamental biological questions about physiological and pathological alterations of the genome, explore broader aspects of epigenetics, and determine the chromatin structure requirement of stem cells and pluripotency. Therefore, GCC is useful for diagnostics and therapy.

Overall Strategy

One of the major limitations of current molecular biology approaches to chromosome conformation study is that their design does not enable capturing all binary contacts throughout the genome. To address this problem, we have devised a method that connects DNA fragments cross-linked through protein complexes with a short DNA linker (the linker can be an external piece of DNA or a modification of the restriction site used to digest chromatin, see below). The resulting library is estimated to be millions of DNA molecules in which a linker connects two DNA fragments. The common linker can then serve as the primer template to analyze the library by massively-parallel sequencing (e.g., Illumina Genome Analyzer/Solexa) and to identify potentially interacting genomic loci joined at each end of the linker. Alternatively, the library can be sequenced from both ends to determine the interacting loci. The second way of the sequencing is of course the only possible way in case of a linker that is a modified restriction site. In principle, such a method can be used to capture the interaction of all genomic elements that are proximal and cross-linked by formaldehyde in vivo. This approach will allow us to detect genome wide binary contact in a high-throughput and unbiased manner. The following is an outline of the GCC protocol and some of the key features of experimental design. The following design is focused on the presence of an external linker, but the elements will be fundamentally the same in case of a modified restriction site linker.

Figure 2:
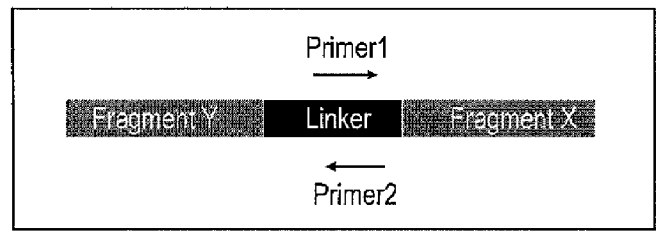
FIG. 2. The strategy to detect locus-locus interactions independent of the sequence of interacting loci. The interacting fragments (X and Y) that were kept in proximity by formaldehyde cross-linking, are connected to each other using a linker DNA. The sequence of the linker is then used as binding site for sequencing primers in the two sequencing reactions that follow. Alternatively, the sequencing can be done from the two ends in an inward direction, rather than from the linker in an outward direction based on the design of that particular reaction.

Step 1: Connecting Genomic Elements Cross-Linked in vivo by a Double-Stranded DNA Linker GCC technology uses formaldehyde to cross-link the chromatin and preserve its topology. The chromatin is then digested with a restriction enzyme to small fragments. Enzymes with smaller cut site sequence are preferred since they produce smaller pieces of the chromatin. Using other enzymatic and non-enzymatic methods (e.g., sonication) is also conceivable for this purpose. For any technology to be able to establish the interaction frequency map and thereby the topology of the entire genome, a mechanism of detection that does not rely on the sequence of interacting loci is essential. To achieve this goal, GCC uses an external DNA element (the linker) or to connect the interacting loci. GCC can also be done without an external linker and by modifying the structure of restriction-digested DNA ends to accommodate certain aspects of library cleaning in later steps (see below). In case of an external linker for the generated library, the sequence of the linker can be used as primer docking site for sequencing of the interacting elements and determination of their identities throughout the entire library (FIG. 2). This reaction takes place at diluted concentrations which favor formation of intramolecular links between DNA fragments cross-linked to each other by formaldehyde through protein intermediates.

Figure 3:
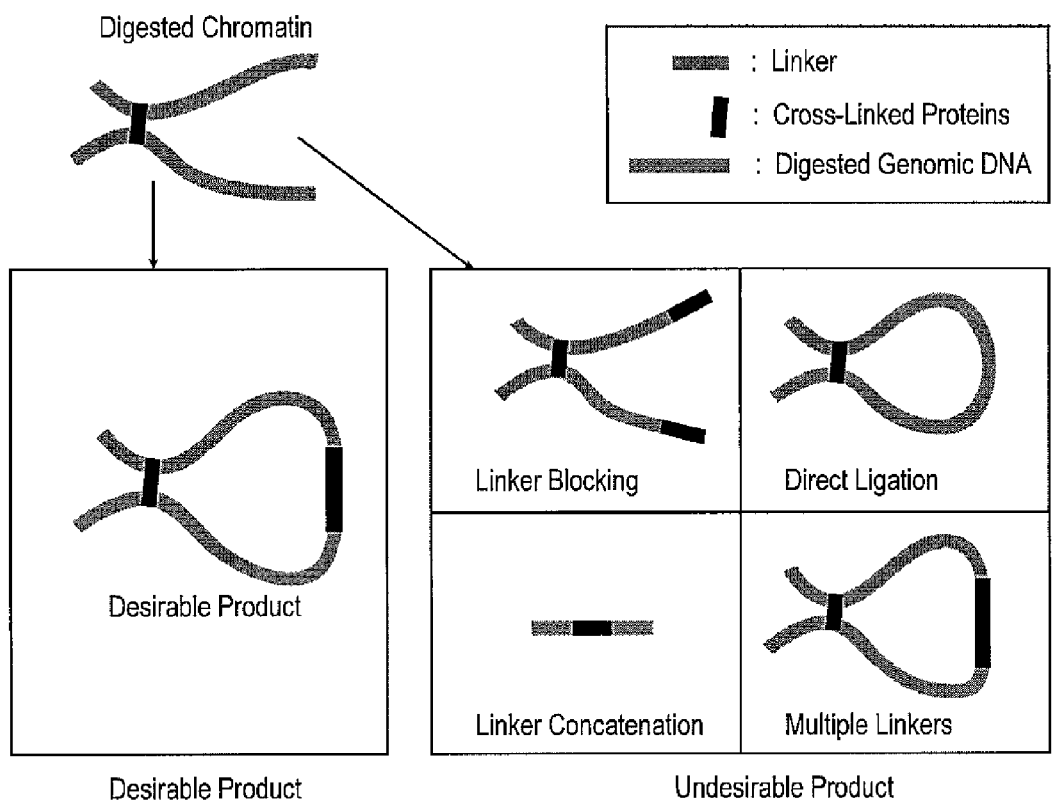
FIG. 3. Problems with a simple linker insertion strategy. The most simple linker insertion strategy results in a high fraction of undesirable products that will present as noise in the sequencing step.

High-efficiency insertion of a DNA linker in between cross-linked DNA fragments is complicated and subject to competition of many side reactions. For example, if the linker is to be inserted as a piece of dsDNA just like a construct is inserted in the vector during the cloning process, it would be impossible to obtain high efficiency. That is because to assure efficient ligation of the linker to DNA ends, high concentration of the linker is required. But high concentration causes a linker to be ligated to each DNA fragment without being able to connect it to the proximal DNA fragment, since the proximal fragment has also been ligated to a linker. At the same time, using low concentration of the linker is not an option since it would significantly reduce the efficiency of the process. FIG. 3 shows some of possible problems that will overwhelmingly reduce the efficiency of this most simple linker-insertion strategy. These and other problems call for a linker-insertion strategy that can overcome most of the challenges associated with the process.

One effective method to successfully insert a linker between cross-linked DNA strands is to introduce the linker in two separate pieces (the half-linkers). Each half-linker is a double-stranded DNA that has a 3' T overhang on one side and a 3' palindromic overhang on the other side (see FIG. 6). A complete linker is formed by two half-linkers joined by their palindromic overhangs. Complete linker is generated in the following manner: half-linkers are ligated to DNA ends generated by restriction digestion of cross-linked chromatin through T:A ligation (other methods of ligation, including blunt-ended ligation and palindromic-overhang ligation may be used depending on the restriction enzyme used.

Figure 4:
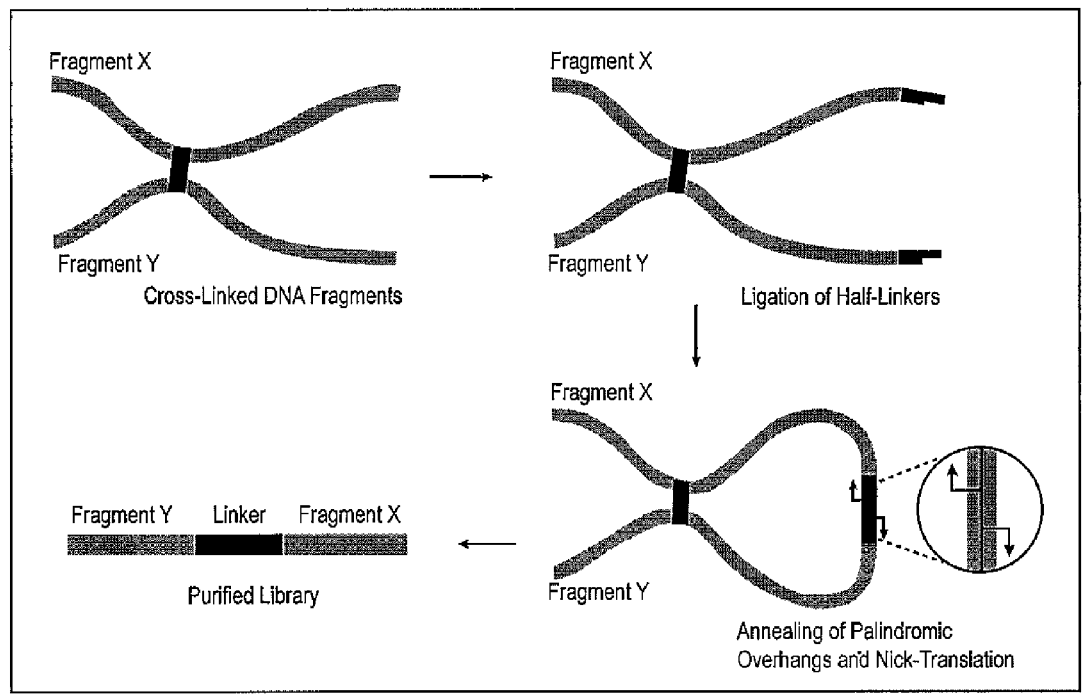
FIG. 4. Linker insertion strategy. Half linkers (brown) are ligated to the ends of cross-linked chromatin DNA fragments. The half-linkers of adjacent cross-linked DNA fragments are fused to form a complete linker by nick-translation. Cross-links are then reversed and DNA is purified to obtain the GCC library.

Then, nick-translation with E. coli DNA polymerase I is carried out at low temperatures (below the annealing temperature of the palindromic overhang) and large volumes to favor intramolecular fusion of half linkers of cross-linked DNA fragments into complete linkers by using the annealed palindromic overhangs as primers (FIG. 4). As explained below, this strategy offers ways to address the challenges associated with effective insertion of a linker between cross-linked DNA fragments.

GCC makes enrichment of DNA molecules with proper insertion of linker between two genomic DNA fragments possible. This is accomplished by incorporation of dATPalphaS (or any other nuclease resistant dNTP analogue, or any other chemical that can confer nuclease resistivity), into target DNA during nick-translation. dATPalphaS can be incorporated to nascent DNA strand by E. coli DNA polymerase I. Insertion of this analogue generates a phosphothioate linkage in DNA in place of phosphodiester bond. Phosphothioate linkage behaves in the exact same manner as a phosphodiester bond except that it is resistant to E. coli Exonuclease III (ExoIII). ExoIII can degrade double-stranded DNA in a 3'→5' direction but it stops after encountering a phosphothioate bond. Any other exonuclease that is unable to break a phosphothioate bond, or any nuclease in combination with any other resistant modification can be used. This way, at the end of linker insertion process and after purification of DNA from cross-linked protein, we treat the sample with ExoIII which degrades all DNA molecules except for those that have incorporated dATPαS in both ends. Only DNA molecules that are a result of fusion of two half-linkers through nick-translation have phosphothioate bonds on both ends and resistant to degradation by ExoIII. This process can effectively enrich the fragments that represent proper insertion of a linker. Biotinylated analogues of nucleotides can also be used in the nick-translation step. In this case, if the biotinylated analogue has been used in conjunction with exonuclease resistant analogue, after treatment with Exonuclease, the target DNA can be further purified using streptavidin (e.g., in form of streptavidin coated beads and surfaces).

If instead of an external linker, a modified restriction site is being used, dATPalphaS will be used in conjunction with Biotinylated nucleotides in modification of the site to produce a DNA molecule that has the biotin closer to the end than dATPalphaS. In this case, after ligation of the ends to each other, a combination of Exonuclease (e.g., *E. coli* exoIII) and streptavidin (e.g., coated beads) can be used to extract target DNA. Only the DNA fragments that have undergone ligation will have biotinylated nucleotides protected from exonuclease (because of being internal rather than terminal biotin). All molecules that have no ligated ends (presumable to another molecule cross-linked to them) will lose biotin at all ends and won't be captured with streptavidin. On the other hand, the molecules that result from the ligation of one DNA fragment to another will remain biotinylated and can be purified.

At the conclusion of Step 1, reversing the cross-links and purifying DNA will result in a library in which DNA fragments that were in close proximity in the intact chromatin are connected to each other through linkers with known sequences, or modified restriction sites that contain modified nucleotides (i.e., bioting and phosphothioate-containing).

Step 2: Sequencing the Cross-Linked Genomic Elements

Figure 5:
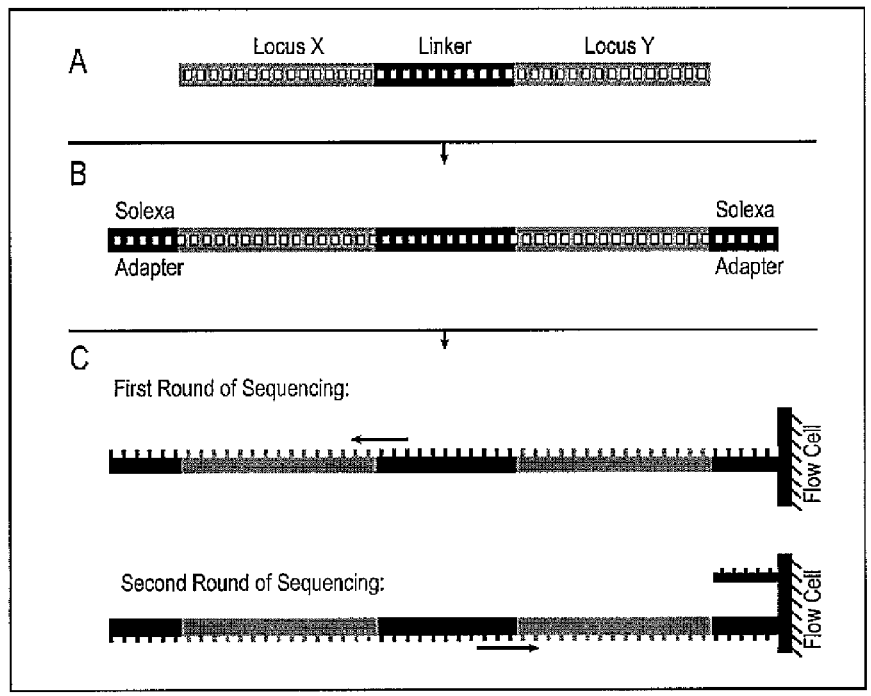
FIG. 5. Schematic representation of GCC sequencing in Illumina Genome Analyzer (Solexa). After linker insertion (A) all of the DNA fragments are ligated to Solexa adaptors (B). These adaptors help immobilize DNA molecules on certain location in the flow cell where sequencing takes place (C). Two consecutive rounds of sequencing by primers that recognize the GCC adaptors produce the read-pair information necessary identify the binary contact. Millions of DNA molecules undergo these steps in parallel.

Sequencing the library obtained in the DNA preparation step described above has unique requirements. Both strands of DNA molecules in the library should be sequenced to obtain the sequence of both DNA fragments connected to one linker (FIG. 2, FIG. 5). It is also essential to know which two sequencing reads belong to the same DNA molecule (a read-pair). Additionally, a very high number of sequencing read-pairs should be generated to cover the entire map of interactions. Ultra-high throughput sequencing that satisfies above requirements has become available recently in the Illumina Genome Analyzer (Solexa) platform. Although in principle other sequencing platforms may be compatible with this process. In the paired-end protocol of this platform (Illumina Inc.), after each DNA molecule is amplified in a cluster on the surface of the chip, one of the two strands is washed away and the other strand is sequenced. Then the complementary strand is re-grown and sequenced after washing away the original strand. This makes it possible to sequence both strands of a DNA molecule while knowing which two reads belong to the same molecule of DNA (FIG. 5). The nearly 80-100 million short sequencing read pairs that are generated in each run of Illumina Genome Analyzer can then be analyzed to obtain the interaction map of the entire genome.

In case of external linker that is sequenced by primers recognizing the linker, the original Illumina Genome Analyzer/Solexa paired-end sequencing protocol has to be modified to conform to GCC. For that the generic primers used in a standard Solexa sequencing reaction. have to be replaced with those complementary to GCC linker sequences. If sequencing is done from the two ends, no modification to the generic paired-end protocol of the Genome Analyzer (Solexa) is required.

Step 3: Devising a Data Analysis Strategy for Sequencing Read Pairs

First the chromosomal location of every sequencing read should be determined. Then a matrix of all binary interaction points should be constructed to obtain a genome-wide binary interaction map. After this point the exact strategy for further analysis will depend on the nature of the data (e.g., coverage and redundancy) and the questions.

Figure 1A:
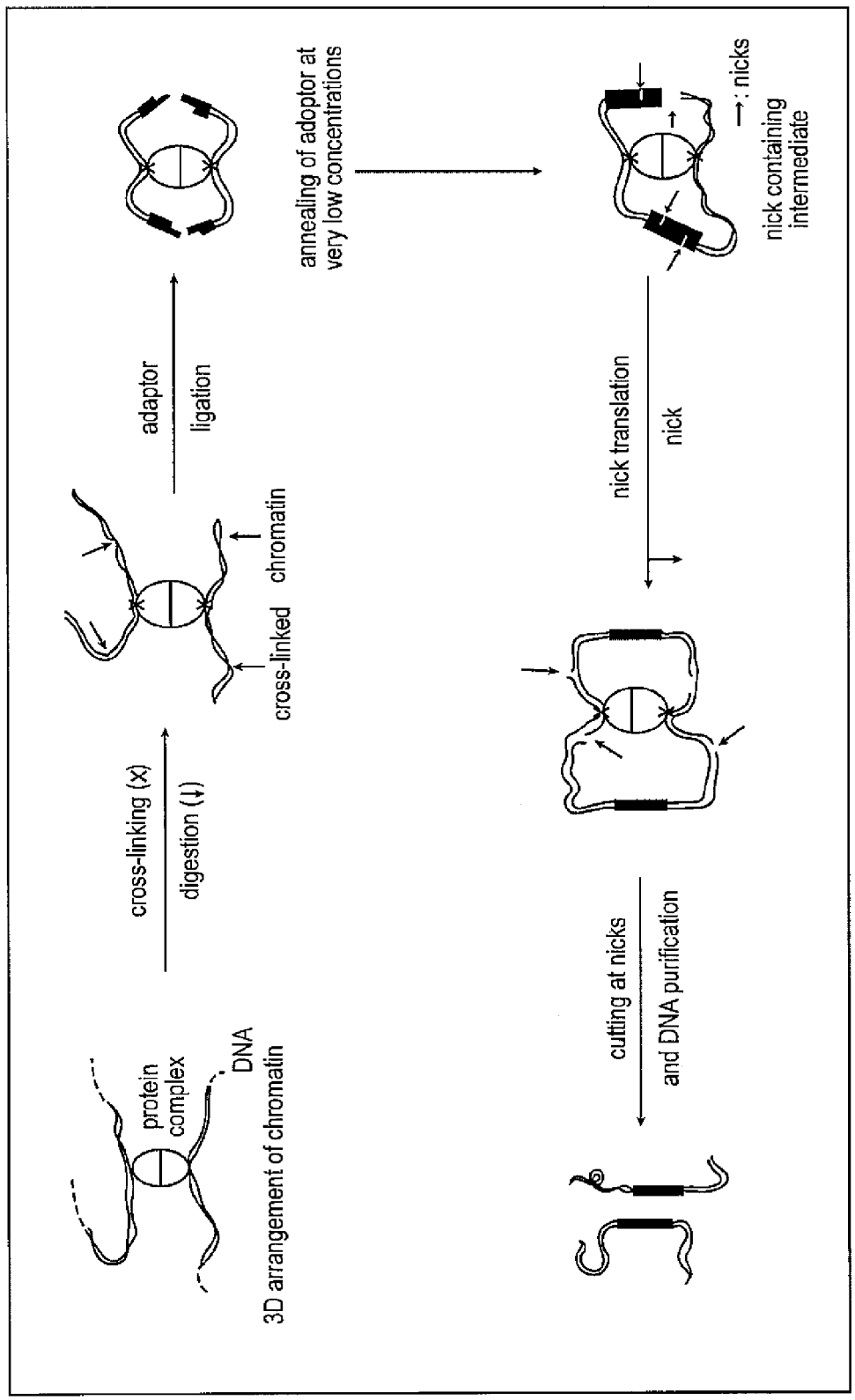
FIG. 1. Schematic representation of G3C.
Figure 1B:
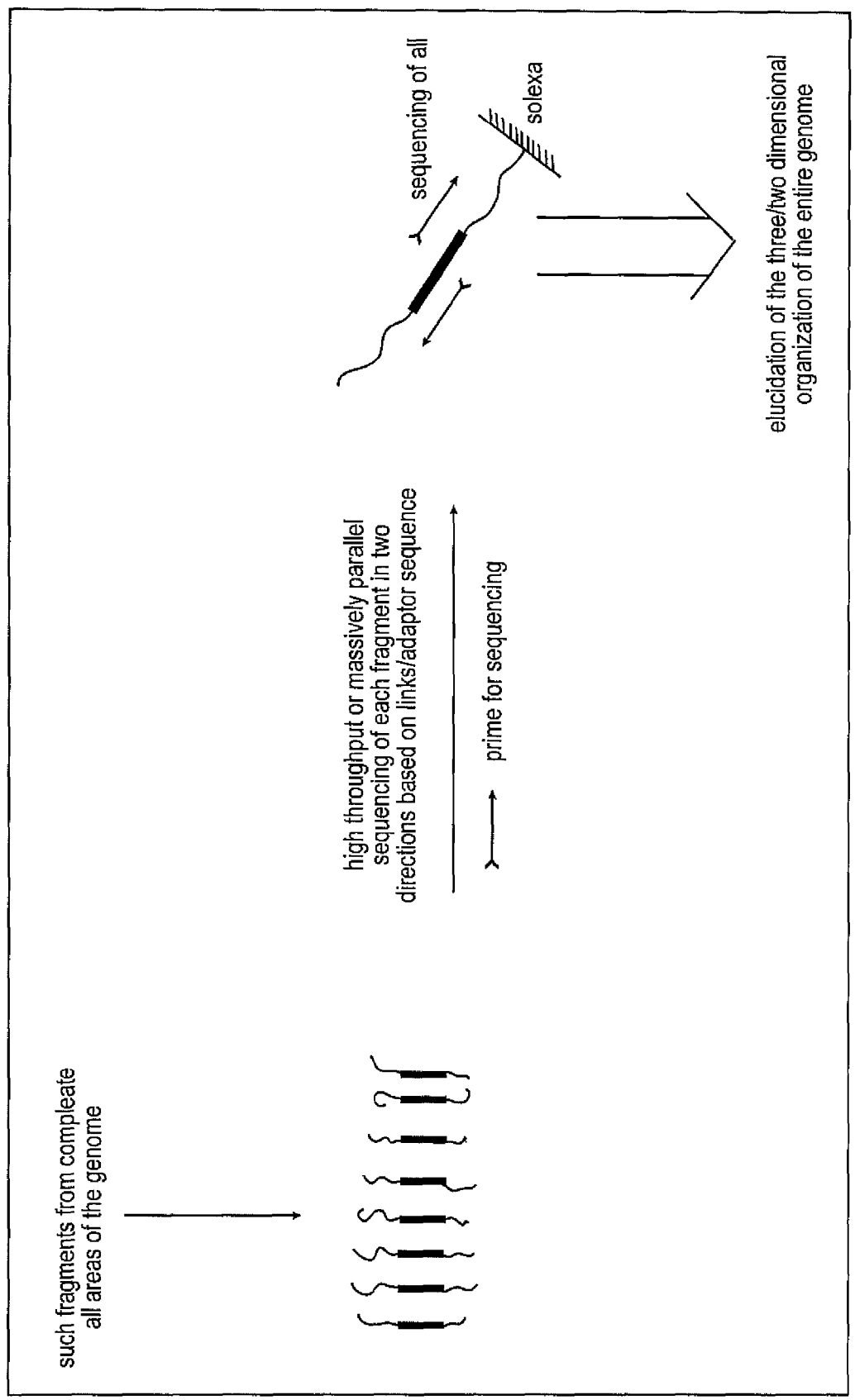

In one embodiment of the invention, chromatin structure is preserved by using a crosslinking reagent, paraformaldehyde. (Methods Enzymol. 2004; 375:493-507). Cells are lysed and chromatin is digested with a restriction enzyme (Methods Enzymol. 2004; 375:493-507) to smaller DNA fragments crosslinked to proteins. DNA linkers (which contain a palindromic overhang on one end and a 'T' overhand on the other end, e.g., as described in the Example below) are ligated to all free DNA ends generated by the restriction enzyme through their 'T' overhang using T4 DNA ligase. The reaction is diluted at this point to concentrations that highly favor intramolecular reactions (Methods Enzymol. 2004; 375:493-507). The longer overhangs of the linkers that are ligated to free DNA ends on one side are annealed to each other. This results in annealing of linkers that are adjacent due to their corresponding DNA fragments being crosslinked to each other through a protein complex (FIG. 1). *E. coli* DNA Polymerase I may be used to carry out nick translation on these annealed linker overhangs to make the connection between crosslinked pieces of DNA permanent (Methods Enzymol. 1987; 152:91-94). Nick translation proceeds from the linker outwards in both directions until it arrives at a crosslinked site. Crosslinked proteins are then detached from the DNA fragments by heating to 65° C. overnight (Methods Enzymol. 2004; 375:493-507). DNA is extracted using phenol:chloroform (Methods Enzymol. 1987; 152: 33-41). The unwanted pieces of DNA that have not gone through proper association with an adjacent DNA fragment and the free non-ligated linker are removed from the reaction using phosphothioate-sensitive exonucleases. This is done by adding phosphothioate containing nucleotides to both ends of properly-linked DNA fragments in a second nick-translation reaction. Only the DNA fragments that have nicks before a crosslinked site on both ends can undergo the second round of nick translation and incorporate phosphothioate containing nucleotides. These DNA fragments are protected from 3'→5' exonuclease action and unwanted pieces of DNA are degraded. The obtained DNA goes through two rounds of massive parallel sequencing (MPS) using the Illumina/Solexa platform. These sequencings are a modification of the Illumina/Solexa "Paired-end Sequencing" protocol (see, e.g., DNA Sequencing brochure at www.illumina.com) in which the two primers for each round of sequencing are based on the linker region added in between two crosslinked DNA fragments and lead to sequencing of the DNA flanking the linker on both sides. This is made possible only by taking advantage of the capability of the Solexa platform to preserve the template location between two rounds of sequencing. As a result, it is possible to determine the pair of sequencing reads that correspond to DNA fragments linked to each other by the one linker. Blasting these sequence read pairs against the linear sequence of the genome provides information about their three dimensional arrangement in the nucleus.

The following example is intended to illustrate, but not to limit, the scope of the invention. While such example is typical of those that might be used, other procedures known to those skilled in the art may alternatively be utilized. Indeed, those of ordinary skill in the art can readily envision and produce further embodiments, based on the teachings herein, without undue experimentation.

EXAMPLE

In this section we briefly describe a GCC experiment that has produced a library with more than 95% DNA molecules with proper insertion of a linker (i.e., molecule that will produce a read-pair in sequencing). Clearly, numerous variations of the protocol below, have, and could produce the same results.

C2C12 mouse fibroblast cells were cross-linked with formaldehyde. Cells were lysed and chromatin was partially denatured with SDS. After treatment with Triton X-100 and addition of digestion buffer, AluI was used to digest the chromatin overnight. AluI is a blunt-cutter and its restriction site (AGCT) occurs once every ~224 by in the mouse genome. On cross-linked chromatin, the average size of the distribution of fragment sizes produced by this enzyme is 500-600 bp.

To carry out T:A ligation after digestion, the terminal transferase activity of exo-Klenow fragment together with dATP were employed to add a 3' A-overhang to blunt ends generated by AluI. The half-linkers that have a T-overhang on one side were ligated overnight to these A-overhang carrying DNA ends. FIG. 6 shows an example of a half-linker used. The T and A-overhangs ensure that genomic DNA ends can only be ligated to half-linker and not to each other and vice versa.

At this point the volume of the reaction was increased 200 times (from 800 microliters to 160 milliliters) which favors intramolecular annealing of the 3' overhangs. To begin annealing and nick-translation, the temperature of the mixture was lowered to a temperature below the Tm of the palindromic overhang (which is ~18 degrees of Celsius) and *E. coli* DNA polymerase I together with the four dNTPs including the exonuclease resistant dATPalphaS and Biotin-dCTP were added to the reaction. This will fuse two proximal half-linkers from cross-linked DNA fragments into a full linker that connects the two fragments to each other (FIG. 4).

The nick-translation process was stopped with addition of EDTA. Treatment with proteinase K and incubation at 65 degrees overnight were used to remove and degrade the cross-linked proteins. The non-enriched library was purified with standard phenol:chloroform extraction.

To enrich the small percentage of DNA molecules that have a linker connecting two DNA fragments, the library was treated with ExoIII which degrades DNA in 3'→5' direction (opposite of nick-translation). Only the molecules that have two fragments on different sides of a full-linker and have incorporated resistance conferring dATPαS through nick-translation in both directions can survive this treatment. Most of the rest will be degraded. After purification, the DNA molecules were mixed with Dynabeads MyOne Streptavidin C1 beads to bind the biotin-containing DNA fragments to the beads and wash away the rest. This results in enrichment of the desirable DNA molecules that carry binary interaction information.

In the end, to assess the success of GCC library preparation, all the contents of the library were amplified through a ligation mediated PCR (LMPCR) carried out on the surface of Streptavidin coated beads (MyOne C1) and cloned into a vector. A number of colonies were selected randomly and sequenced with standard chain-termination chemistry. 95% of the library contained a proper insertion of a full-linker in between two DNA fragments. FIG. 7 shows selected examples of DNA molecules obtained in this experiment.

These results demonstrate the feasibility of GCC library preparation to connect two loci in physical proximity in the structure of nucleus with a DNA linker. Similar results have been obtained using modified restriction sites as linkers rather than using external linkers.

REFERENCES

1. Science 1998; Apr. 24; 280(5363):547-53.
2. Science 2002; 295(5558):1306-11.
3. Spilianakis CG et al. Nature 2005; 435(7042):637-45.
4. Dostie J et al. Genome Res. 2006; 16(10):1299-309.
5. Simonis M et al. Nat Genet. 2006; 38(11):1348-54.
6. Zhao Z et al. Nat Genet. 2006; 38(11):1341-7.
7. Methods Enzymol. 2004; 375:493-507.
8. Methods Enzymol. 1987; 152:91-94.
9. Methods Enzymol. 1987; 152:33-41.

All publications cited herein are incorporated by reference in their entirety.

---

What is claimed is:

1. A method of determining the three-dimensional arrangement of an entire genome in a cell, comprising:
   (a) contacting a cell with a cross-linking reagent to cross-link the chromatin and the proteins in the cell;
   (b) lysing the cell;
   (c) digesting the chromatin with a restriction enzyme to generate DNA fragments with free ends, wherein the DNA fragments are cross-linked to the proteins;
   (d) ligating DNA linkers to all free DNA ends generated by the restriction enzyme;
   (e) annealing the ends of the DNA linkers that are not ligated to the free DNA ends generated by the restriction enzyme;
   (f) translating the nicks between the annealed ends of the DNA linkers;
   (g) detaching the proteins cross-linked to the DNA fragments;
   (h) extracting DNA;
   (i) subjecting the extracted DNA to two rounds of parallel sequencing; and
   (j) determining the three-dimensional arrangement of the entire genome in the nucleus of the cell.

2. The method of clam 1, wherein the cross-linking reagent is formaldehyde.

3. The method of claim 1, wherein the DNA linkers contain a palindromic overhang on one end and a T overhang on the other end.

4. The method of claim 3, wherein the DNA linkers are ligated to the free DNA ends generated by the restriction enzyme through the T overhang.

5. The method of claim 3, wherein the DNA linkers are ligated to the free DNA ends generated by the restriction enzyme by T4 DNA ligase.

6. The method of claim 1, further comprising adjusting the ligation mixture after step (d) to highly favor intramolecular reactions.

7. The method of claim 1, wherein the ends of the DNA linkers being annealed in step (e) are adjacent due to the DNA linkers being ligated to the DNA fragments that are cross-linked to the proteins.

8. The method of claim 1, wherein the nicks are translated with *E. coli* DNA polymerase I.

9. The method of claim 1, wherein the nicks are translated in both directions along the DNA fragments until they arrive at cross-linked sites.

10. The method of claim 1, further comprising adding phosphothioate-containing nucleotides to a second round of nick-translation.

11. The method of claim 1, wherein the proteins cross-linked to the DNA fragments are detached by heating at 65° C. over night.

12. The method of claim 1, wherein the DNA is extracted with phenol:chloroform.

13. The method of claim 1, further comprising removing DNA that has not gone through steps (d) and (e) and free DNA linkers after step (h).

14. The method of claim 13, wherein the DNA that has not gone through steps (d) and (e) and free DNA linkers are removed by a phosphothioate-sensitive exonuclease.

15. The method of claim 1, wherein the extracted DNA is sequenced using the Illumina/Solexa platform.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 1
gcagatcaat taatacgata cctgcggacc ggtc                              34

<210> SEQ ID NO 2
<211> LENGTH: 27

```
<212> TYPE: DNA
<213> ORGANISM: Artificial Sequence
<220> FEATURE:
<223> OTHER INFORMATION: Synthetic oligonucleotide

<400> SEQUENCE: 2
tcgtctagtt aattatgcta tggacgc                                              27
```